United States Patent [19]
Sproat et al.

[11] Patent Number: 5,658,731
[45] Date of Patent: Aug. 19, 1997

[54] 2'-O-ALKYLNUCLEOTIDES AS WELL AS POLYMERS WHICH CONTAIN SUCH NUCLEOTIDES

[75] Inventors: Brian Sproat, Heidelberg; Angus Lamond, Wiesenbach, both of Germany

[73] Assignee: Europaisches Laboratorium fur Molekularbiologie, Heidelberg, Germany

[21] Appl. No.: 376,697

[22] Filed: Jan. 23, 1995

Related U.S. Application Data

[63] Continuation of Ser. No. 941,078, filed as PCT/EP91/00665 Apr. 8, 1991, abandoned.

[30] Foreign Application Priority Data

Apr. 9, 1990 [DE] Germany .................. 40 11 473.2

[51] Int. Cl.$^6$ .................. C12Q 1/68; C07H 19/06; C07H 19/16; C07H 21/00
[52] U.S. Cl. .................. 435/6; 536/23.1; 536/24.3; 536/26.1; 536/26.2; 536/26.23; 536/26.26; 536/27.1; 536/27.21; 536/28.4
[58] Field of Search .................. 536/23.1, 23.2, 536/24.1, 24.3, 24.31, 24.5, 25.3, 27.21, 27.6, 27.8, 27.81, 28.4, 28.5, 28.53, 28.54, 26.11, 26.13, 26.2, 26.23, 26.26; 435/6, 91.31, 172.1, 172.3, 240.2; 514/44

[56] References Cited

FOREIGN PATENT DOCUMENTS

| 0260032 | 3/1988 | European Pat. Off. . |
|---|---|---|
| 8912642 | 12/1989 | WIPO . |

OTHER PUBLICATIONS

Reimann et al. (1983) J. Protein Chem vol. 1(2):113–129.
Sproat et al. (1990) Nuc Acid Res vol. 18(1):41–49.
Sproat et al. (1991) Nuc Acid Res vol. 19(4):733–892.
Anisuzzaman et al. (1990) Polyhedron vol. 9(6):891–892.
Stein et al. (1993) Science, vol 261: 1004–1012.
Wagner et al "Antisense Gene Inhibition by Oligonucleotides . . . " Science 260 (Jun. 1993), pp. 1510–1513.
Gura "Antisense has Growing Pains" Science 270 (Oct. 1995), 575–577.
Milligan et al "Current Concepts in Antisense Drug Design" J. Med. Chem 36 (Jul. 1993), 1923–1937.
Zon et al "Phosphorothioate Oligonucleotides" in *Oligonucleotides and their Analogues* IRL Press (F. Eckstein Ed) 1991 pp. 87–108.
Sproat "Synthesis of 2'–O–Alkyloligoribonucleotides" in *Meth in Molecular Biol.* 20 (1993), 115–116 inclusive.
Nucleic Acids Research, (1989) vol. 17, No. 9, pp. 3373–3386.
Nucleic Acids Research, (1987) vol. 15, No. 15, pp. 6131–6148.
Chemical Abstracts, (1991) vol. 114, p. 830. 164721j.
Iribarren, A.M., et al. (1990) Pro. Natl. Acad. Sci. USA vol. 87, pp. 7747–7751.

*Primary Examiner*—John L. LeGuyader
*Assistant Examiner*—Thomas G. Larson
*Attorney, Agent, or Firm*—Felfe & Lynch

[57] ABSTRACT

Oligonucleotides having the general formula, in which

B denotes an arbitrary nucleobase,

A equals 0 or $CH_2$;

X or Z equals O, S, NH or denotes $CH_2$ whereby X and Z can be the same or different, V and W denote O, S, Se, $NH_2$ or an alkyloxy residue, or OH or SH whereby V and W can be the same or different in a monomer unit and L is a H atom or a partner of a binding pair and C equals —O—R and R is an alkyl group with at least 1 C atom which may be modified if desired, or it denotes an alkenyl or alkynyl group with at least 2 C atoms which may be modified if desired, whereby the modification consists of a substitution by one or several halogen, cyano, carboxy, hydroxy, nitro or/and mercapto residues, and n is an arbitrary whole number, are stable antisense probes which bind specifically. Such oligonucleotides and polynucleotides may be used for the regulation of gene expression and as pharmaceutical agents. They are synthesized from the corresponding 2'-substituted monomers according to well-known methods, preferably on a solid phase.

23 Claims, No Drawings

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i i ) MOLECULE TYPE: nucleic acid ( i x ) FEATURE:
        ( A ) NAME/KEY: N = inosine ( x i ) SEQUENCE DESCRIPTION: SEQ ID NO: 1:

ANAACANAUA CUACACUUNA    20

2'-O-ALKYLNUCLEOTIDES AS WELL AS POLYMERS WHICH CONTAIN SUCH NUCLEOTIDES

This application is a continuation of application Ser. No. 07/941,078, filed as PCT/EP91/00665 Apr. 8, 1991, abandoned.

The invention concerns new nucleotide monomers as well as oligonucleotides and polynucleotides which contain such monomers, a process for their production and their use for regulating gene expression as antisense probes and as pharmaceutical agents.

Antisense oligonucleotides and polynucleotides are known to one skilled in the art and are described in summary for example in "Spektrum der Wissenschaft" (1990), pages 70 to 77. These are understood as the nucleotides which are complementary to the actual gene and have a sequence with the opposite orientation. Such antisense molecules act on gene expression in a regulatory manner and in so doing play an important role in determining whether a hereditary sequence coded in gene is translated into an protein. In this process the separation of the two DNA strands is triggered by a short RNA chain, the so-called primer, which first opens up the DNA double helix and hybridizes with the origin of replication. It has been shown that the gene expression depends not only on the concentration of these primer molecules but on their ratio to the antisense RNA. In this manner it is therefore possible to switch predetermined genes on and off specifically and thus to regulate the entire cell function. Thus for example cells which have been malignantly transformed by means of a polyoma virus appear healthy by introducing expression vectors for an antisense RNA against src into these polyoma transformed cells. By this means these cells loose their cancerogenic characteristics. Similar results with this antisense technique have already been achieved on the oncogenes fos, ras and sys. Moreover it has already even been possible to inhibit infections by herpes viruses, influenza viruses and the HIV virus in tissue cultures using antisense oligonucleotides. With the aid of biotinylated antisense oligonucleotides it has also been possible to investigate the formation and action of the splicing complex in more detail (S. Barabino, B. Sproat et al., The EMBO Journal 8, 4171-4178 (1989). The 5'-biotinylated oligonucleotides have at their 5'-terminus four 2'-deoxycytidine residues that have been modified to carry biotin groups linked via an amino alkyl spacer on the exocyclic amino group of the cytidine ring. In the 3'-biotinylated oligonucleotides four biotin molecules were linked through a similar spacer arm to four modified uridine residues.

However, the antisense oligonucleotides and polynucleotides known up to now have the disadvantage that after being introduced into an intact cell they are attacked and degraded by RNA- and DNA-specific nucleases which leads to a loss in their activity. Previous attempts have been made to inhibit the degradation of polynucleotides and oligoribonucleotides by nucleases by means of 2'-O-methyl substitution (B. Sproat et al., Nucleic Acids Research 17 (1989), 3373–3386).

Therefore the object of the invention is to provide new oligonucleotides and polynucleotides which are resistant to attack by nucleases and which bind to a complementary nucleotide strand with improved specificity.

In the surprising finding of the invention this object can be achieved by substituting the 2' position with an alkyloxy group having at least two carbon atoms.

The invention therefore concerns nucleopolymers based on 2'-O-alkylnucleotides having the general formula II

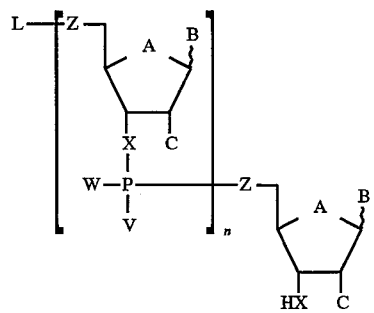

in which

B represents an arbitrary derivative known to one skilled in the art of any nucleoside base and in particular an adenine-9-yl (A), a cytosine-1-yl (C), a guanine-9-yl (G), a uracil-1-yl (U), a hypoxanthine-9-yl (I) or a thymine-1-yl group (T). Of the adenine derivatives the 2-aminoadenine-9-yl residue is preferred. It is expedient that one or several of the nucleoside bases carry a substituent L which facilitates attachment to particular parts of the cell or to enzymes or also to suitable chromatographic material. Such affinity substituents are known to one skilled in the art.

A denotes an O atom or a $CH_2$ group,

X or Z represent an O atom, a S atom, a NH or $CH_2$ group and can be the same or different, V and W represent an O, S or Se atom or represent an —OH, —SH, —$NH_2$, alkyl or alkyloxy group. Preferred alkyl and alkyloxy groups have 1 to 4 carbon atoms and are in particular —$CH_3$, $C_2H_5$ and/or $OCH_3$ or $OC_2H_5$. In a monomer unit in the oligonucleotides and polynucleotide according to the present invention V and W can be the same or different.

L represents an H atom or a partner of a binding pair.

C denotes a group having the general formula —O—R in which R is an alkyl group with at least 1 C atom which may modified if desired, or an alkenyl or alkynyl group with at least 2 C atoms which may be modified if desired, whereby the modification consists of a substitution by one or several halogen, cyano, carboxy, hydroxy, nitro or/and mercapto residues. The alkyl group preferably has 3 to 6 carbon atoms and in particular 3 or 4 carbon atoms. Examples of particularly suitable alkyl groups are propyl and butyl, however, modified alkyl groups such as cyanomethyl are also preferred. Alkenyl chains are particularly preferred and in particular alk-2-enyl residues of which in turn an allyl residue is preferred. The propargyl residue may be mentioned as example of an alkynyl group.

Preferred polymers according to the present invention have one or several of the monomer units previously described, if desired in combination with other monomer units in which —O—R equals —O-allyl, A equals O, X equals O, Z equals O, W equals O and V equals OH and the C1 carbon atom of the sugar is in the β-configuration. In a further preferred embodiment the oligonucleotides and polynucleotides according to the present invention have a 3'-deoxyribonucleoside at their 3' end which inhibits attack by 3' exonucleases and additionally impedes degradation by these enzymes.

By incorporating a partner of a binding pair, e.g. selected from the pairs antibody/antigen or biotin/avidin or streptavidin, preferably biotin or a dinitrophenyl residue into the polymer according to the present invention it is possible to immobilize the nucleotide polymer according to the present invention and to carry out an affinity chromatography of proteins, nucleic acids and/or protein/nucleic acid complexes which bind to the immobilized nucleotide polymer.

the state of the art they have a reduced non-specific binding to nucleic acid binding proteins.

However, the invention also concerns nucleotide monomers which are suitable for the synthesis of the oligonucleotides and polynucleotides according to the present inven-

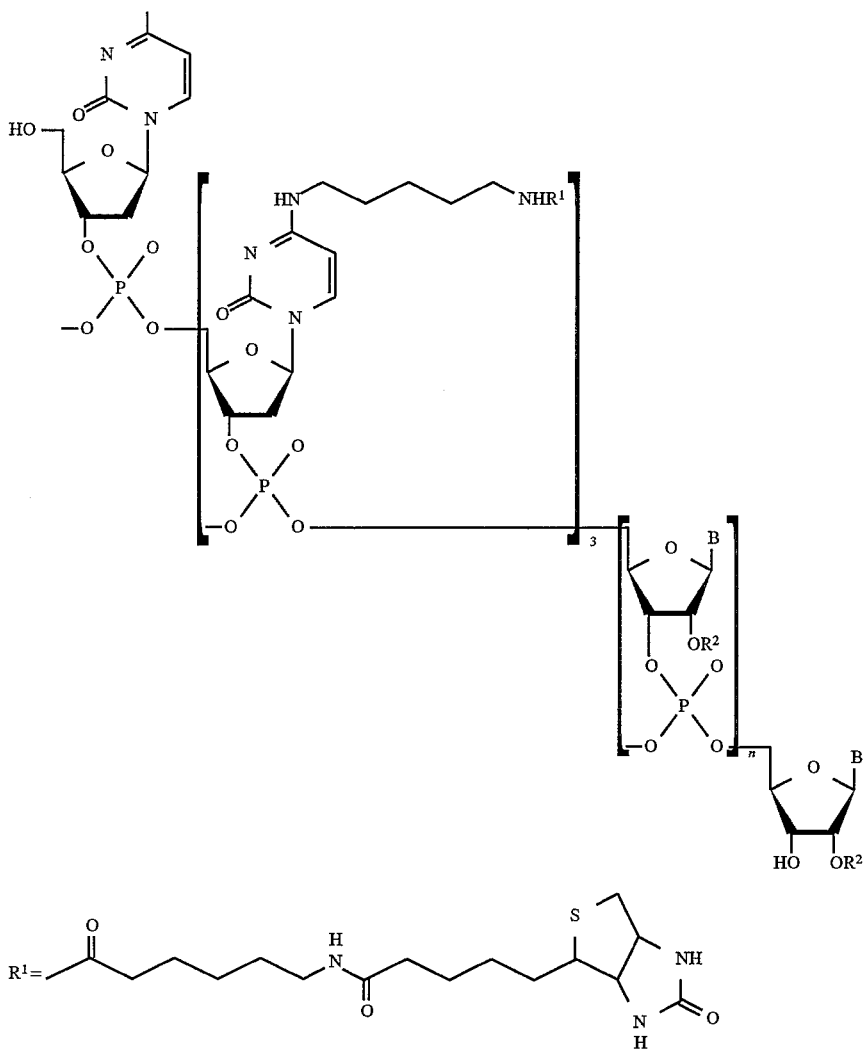

$R^2 =$ —$CH_3$(methyl), or —$CH_2$—$CH=CH_2$(allyl), or —$CH_2$—$CH=C(CH_3)_2$(3, 3-dimethylallyl)

above is shown the general structure of 2'-o-alkyl oligoribonucleotides. The structures of the three 2'-o-linked alkyl groups tested, methyl, allyl and 3,3-dimethylallyl are shown as $R^2$. For biotinylated probes (as illustrated), a long-chain biotin derivative ($R^1$) was attached to an aminoalkyl spacer arm, linked to the exocyclic amino group of the non-base-pairing 2'-deoxycytidines. By appropriate incorporation of such modified cytidines, biotin can be placed at either the 5' or the 3' terminus as required. To facilitate 5' end-labeling of 5'-biotinylated oligonucleotides, an additional, nonbiotinylated 2'-O-methyluridine was routinely placed at the 5' terminus. (per Iribarren et al. PNAS (1990) 87:7747–51 at 7747).

A feature of the oligonucleotides according to the present invention is their excellent hybridization to nucleic acids that have a corresponding target sequence which is complementary to them and that they are particularly inert towards degradation by nucleases which is why they have a high biological half-life in living cells. Moreover, compared to tion and which have in the 2' position of the sugar moeity an alkyloxy, alkenyloxy or alkynyloxy residue with at least one carbon atom which, if desired, is modified by one or several halogen, cyano, carboxy, hydroxy, nitro or/and mercapto residues.

Particularly preferred residues are O-alk-2-enyl residues and in particular O-allyl residues. Such a monomer usually has the general formula I

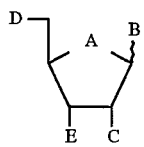

in which A, B and C have the meanings defined above and D and E are reactive groups capable of forming 3'-5' internucleotide-bonds or denote a —$PO_4H_2$, —$P_2O_7H_3$ or —$P_3O_{10}H_4$ group. Such groups are known to one skilled in the art and are for example described in B. Sproat et al., Nucleic Acids Research 18 (1990), 41–49 as well as comprehensively in E. L. Winnacker, "Gene und Klone", VCH Verlagsgesellschaft mbH, Weinheim (Germany) (1985), in particular pages 44 to 49 and in Froehler/Matteucci Tetrahedron Lett. (1986), p. 469–472. The OH group is particularly preferred as the reactive group. The —$PO_4H_2$, —$P_2O_7H_3$ and the —$P_3O_{10}H_4$ group are also preferred as D and/or E. These mono-, di- or triphosphates, or salts of the compounds having the general formula I can be preferably incorporated as 5'-triphosphates into growing nucleic acid chains for example enzymatically using DNA/RNA polymerases (c.f. e.g. Random priming, Anal. Biochem. 132 (1983) 6–13, Nick translation, J. Mol. Biol. 113 (1977) 237–251). Using the reactive mononucleotides according to the present invention it is possible to produce in a known way the oligonucleotides and polynucleotides which are also according to the present invention in particular on a solid phase. The production of such polynucleotides from the corresponding mononucleotides is known to one skilled in the art and is for example also described in more detail in the above-mentioned literature references. The invention therefore also concerns a process for the production of oligonucleotides and polynucleotides using the nucleotide monomers according to the present invention.

Finally the invention also concerns the use of the oligonucleotides and polynucleotides obtained according to the present invention as antisense probes and as pharmaceutical agents in particular as pharmaceutical agents for the treatment of cells infected with viruses such as e.g. the herpes, influenza or the AIDS pathogen as well as for the regulation of gene expression.

The invention is elucidated in more detail by the following examples.

EXAMPLE 1

2'-O-allyl-oligoribonucleotides and 2'-O-methyl-oligoribonucleotides, each having an identical sequence, were produced by the phosphoramidite method according to the process described by B. Sproat, B. Beijer and A. Iribarren in Nucleic Acids Research, Vol. 18 (1990) 41–49. The chosen starting material 2-amino-6-chloropurine was first protected with the Markiewicz disiloxane reagent (J. Chem. Res. (1979) S, 24–25) as illustrated in the reaction scheme below to give compound I in 67 to 74% yield. This was then converted into the highly versatile 2,6-dichloropurine riboside derivative II (below) in 82% yield using the non-aqueous diazotisation procedure of Robins and Uznanski (Can. J. Chem. (1981) 59:3608–3611) using t-butyl nitrite and antimony trichloride in 1,2-dichloroethane at low temperature. During the diazotisation reaction the 2'-hydroxyl group was temporarily blocked as its trimethylsilyl ether, which was subsequently cleaved by a 2 min treatment with p-toluenesulphonic acid, without damage to the disiloxane moiety. The 2-bromo analogue of compound II could also be obtained in a similar yield. The 2-iodo analogue of compound II could also be made in a similar fashion giving the possibility of forming a carbon-carbon bond at the 2-position using the synthetic procedures described by Nair et al. (J. Am. Chem. Soc (1987) 109:7223–7224 and J. Chem. Soc. Chem. Commun. (1989) 878–879). II could be achieved using one equivalent of each of methyl iodide and the sterically hindered strong organic base 2-tert.-butylimino-2-diethylamino-1,3-dimethylperhydro 1,3,2-diazaphosphorin (BDDDP), a reagent first described by Schwesinger (Chimia (1985) 39:269–272), and proceeded in excellent yield when the 6-chloro substitutent was replaced by the bulky 2,6-dichlorophenoxy substituent prior to the alkylation. No observable N-7 alkylation was observed and ring opening of the disiloxane bridge was minimal.

In complete contrast the silver oxide catalyzed methylation (Chem. Pharm. Bull. (1965) 13:1273–1278) route applied to compound II resulted in mostly N-alkylation (even with the 2,6-dichlorophenoxy derivative). Use of limited amounts of methyl iodide and silver oxide gave about a 30% yield of compound III after a reaction time of nearly 2 weeks. The combination of BDDDP and alkyl halide in acetonitrile has enabled us to prepare a variety of 2'-O-alkyl ribonucleoside derivatives in excellent yield.

Compound III is also extremely versatile since the 6-substituent is much more readily displaced by nucleophiles than is the 2-substituent. For instance treatment of compound III with 2-nitrobenzaldoximate gave the disiloxane protected 2'-O-methyl-2-chloroinosine in moderate yield (50–55%), and treatment with methanolic ammonia gave a good yield of disiloxane protected 2'-O-methyl-2-chloroadenosine. Initially, we had hoped to convert the 2-chlorohypoxanthine moiety to the guanine moiety using hydrazine followed by Raney-nickel cleavage of the 2-hydrazino function, however, this method proved rather unreliable and overall yields were poor. Instead, compound III was treated with 2.5 equivalents of sodium azide in DMF at 50° C. to give an excellent yield of 3',5'-O-(tetraisopropyldisiloxane-1,3'diyl)-2'-O-methyl-2,6-diazidopurine riboside. This material was reduced in quantitative yield to give the 2,6-diaminopurine compound IV using Lindlar catalyst poisoned with quinoline. Subsequent desilylation gave crystalline 2'-O-methyl-2,6-diaminopurine riboside (V) in 87% yield.

This compound was then quantitatively converted to 2'-O-methylguanosine, VI, using adenosine deaminase as described by Robins (Can. J. Chem. (1981) 59:3360–3364). The enzyme from calf intestinal mucosa is capable of handling a variety of substrates, and deaminates 2,6-diaminopurine riboside at 29% of the rate for adenosine, the normal in vivo substrate (Biochem. Biophys. Acta. (1965) 99:442–451). In order to avoid the transient protection procedure (J. Am. Chem. Soc. (1982) 104:1316–1319) we decided to block the exocyclic amino group of 2'-O-methylguanosine by an amidine moiety (J. Amer. Chem. Soc. (1986) 108:2040–2048). Thus 2'-O-methylguanosine was reacted with N,N-dimethylformamide dimethyl acetal followed by dimethoxytrityl chloride to give compound VII in excellent yield. Subsequent phosphitylation (Nucleic Acids. Res. (1984) 12:4539–4557) of compound VII gave the pure 2'-O-methylguanosine building block VIII in good yield.

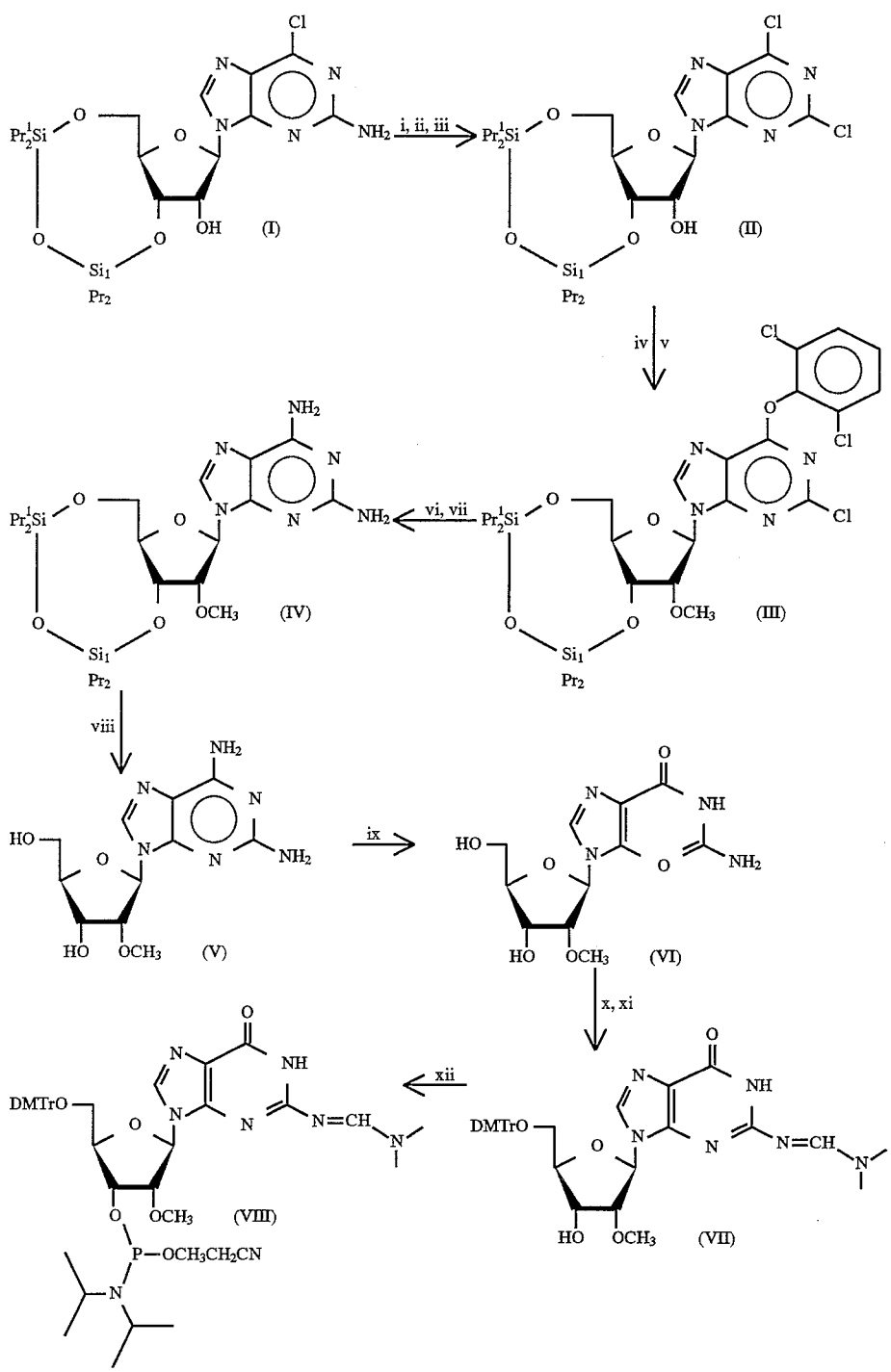

Above is the Reaction Scheme for the synthesis of the 2'-O-methylguanosine building block. Reagents: i, chlorotrimethylsilane and triethylamine in dichloroethane; ii, t-butyl nitrite and antimony trichloride in dichloroethane at −14° C.; iii, p-toluenesulphonic acid in dioxan/dichloromethane; iv, 2,6-dichlorophenol, triethylamine and 1,4-diazabicyclo [2.2.2] octane in dichloroethane; v, methyl iodide and 2-tert.-butylimino-2-diethylamino-1,3-dimethylperhydro 1,3,2-diazaphosphorin in acetonitrile; vi, sodium azide in N,N-dimethylformamide at 50° C.; vii, hydrogen/Lindlar catalyst in ethyl acetate containing quinoline; viii, tetrabutylammonium fluoride in tetrahydrofuan; ix, adenosine deaminase in aqueous phosphate buffer pH 7.4/dimethylsulphoxide; x, N,N-dimethylformamide dimethylacetal in methanol; xi, 4,4'-dimethoxytrityl chloride and triethylamine in pyridine; xii, 2-cyanoethoxy N,N-diisopropylaminochlorophosphine and N,N-diisopropylethylamine in dichloroethane. Subsequently both probes labelled with $^{32}$P-phosphate at their 5' end were incubated with a nuclear extract which was obtained from Hela cells as described by A. Lamond et al. in Cell, Vol. 58 (1989), 383–390. Both probes were then subjected to gel chromatography. It turns out that the 2'-O-allyl-oligonucleotides according to the present invention have an extraordinarily high specific binding activity and a negligible non-specific binding activity in comparison with the 2'-O-Me-oligonucleotides which are part of the state of the art.

The nucleotide sequence was

5'-AIAACAIAUACUACACUUIA 3'   (SEQ ID NO 1)

It binds to human U2 RNA.

EXAMPLE 2

Various nucleases were added to the 2'-O-allyl-oligoribonucleotides produced according to example 1 and their sensitivity to enzymatic degradation was determined. In comparison to normal non-modified RNA with an identical sequence it turned out that on digestion with pancreatic RNase A, RNase CL-3, RNase T1, RNase T2 and RNase U2 the 2'-O-allyl-oligonucleotides according to the present invention are completely resistant to enzymatic attack by nucleases whereas in contrast natural RNA is completely degraded in all cases.

EXAMPLE 3

3',5'-O-(tetraisopropyldisiloxan-1,3-diyl)-2-chloro-6-(2,6-dichlorophenoxy)purine riboside (A) was synthesized as described by Sproat, B. S., Beijer, B. and Iribarren, A., Nucleic Acids Research, 1990, 18, 41–49. The compound A obtained in this way was then allylated as described below. Synthesis of 3',5'-O-(tetraisopropyldisiloxan-1,3-diyl)-2'-O-allyl-2-chloro-6-(2,6-dichlorophenoxy)purine riboside (B):

Tris(dibenzylidene-acetone)dipalladium (O) (174 mg, 0.19 mmol) and 1,4-bis (diphenylphosphine)butane (324 mg, 0.76 mmol) were suspended in dry tetrahydrofuran (50 ml). A solution of compound A (13.11 g, 19 mmol) and allylethylcarbonate (4.95 g, 38 mmol) in 50 ml dry tetrahydrofuran was added and the mixture was heated for 30 minutes under reflux. Silica gel t.l.c. in petroleum ether/ethyl acetate (2:1 v/v) showed a complete reaction with a single UV-positive spot of $R_f$ 0.54 (compound A has an $R_f$ 0.41). The solvent was removed in a vacuum and a red syrup remained which was dissolved in petroleum ether/ethyl acetate (9:2 v/v) and the solution was filtered in order to remove the insoluble Pd-phosphine complex. The product was purified by preparative liquid chromatography on silica gel and eluted with petroleum ether/ethyl acetate (9:2 v/v). The pure compound B was obtained in this manner in the form of a light yellow foam (12.4 g, 89.4%). $^{13}C$ NMR spectrum (CDCl$_3$) δ: 158.12 (C6), 153.13 and 152.54 (C-2 and C-4), 144.66 (phenyl C-1), 142.43 (C-8), 133.75 (—CH= of allyl), 128.77 (phenyl C-2 and C-6), 128.52 (phenyl C-3 and C-5), 127.12 (phenyl C-4), 120.51 (C-5), 117.0 (=CH$_2$ of allyl), 88.26 (C-1'), 81.16 (C-4'), 80.6 (C-2'), 71.4 (O—CH$_2$— of allyl), 69.54 (C-3'), 59.61 (C-5'), 17.19–16.63 (isopropyl CH$_3$s), 13.16, 12.70 and 12.29 p.p.m. (isopropyl CHs).

Compound B was converted further via various steps into the corresponding nucleotide monomer, namely 5'-O-dimethoxytrityl-N$^2$-dimethylaminomethylidene-2'-O-allylguanosine-3'-O-(2-cyano-ethyl-N,N-diisopropylphosphoramidite) using the method described in Nucleic Acids Research, 1990, 18, 41–49.

Monomers were converted into polymers as described in Nucleic Acids Research, 1989, 17, 3373–3386.

EXAMPLE 4

Synthesis of 3',5'-O-(tetraisopropyldisiloxan-1,3-diyl)-2'-O-propargyl-4-O-(2,6-dichlorophenyl)uridine (C):

3',5'-O-(tetraisopropyldisiloxan-1,3-diyl)-4-O-(2 6-dichlorophenyl)uridine (18.95 g, 30 mmol) was dried in a vacuum by evaporation of acetonitrile. The remaining foam was dissolved in anhydrous acetonitrile (50 ml), a 80% by weight solution of propargyl bromide in toluene (3.56 ml, 33 mmol) followed by 2-tert.-butylimino-2-diethylamino-1,3-dimethylperhydro-1,3,2-diazaphosphorine (9.55 ml, 33 mmol) were added while stirring and excluding humidity. Silica gel t.l.c. in hexane/ethyl acetate (2:1 v/v) showed a complete reaction after 5 hours with a UV-absorbing product spot of $R_f$ 0.38. The solvent was removed in a vacuum leaving behind a cream-coloured foam. The product was purified by preparative liquid chromatography using petroleum ether/dichloromethane/ethyl acetate (8:2:1 by volume) as an eluant. The pure product C was obtained as a white foam (10.7 g, 53.3%). $^{13}C$ NMR spectrum (CDCl$_3$) δ: 169.80 (C-4), 154.60 (C-2), 144.76 (phenyl C-1), 144.41 (C-6), 128.69 (phenyl C-2 and C-6), 128.65 (phenyl C-3 and C-5), 127.08 (phenyl C-4), 93.80. (C-5), 89.80 (C-1'), 81.70 (C-2'), 80.34 (C-4'), 79.54 (—C≡ of propargyl), 74.63 (≡CH of propargyl), 67.63 (C-3'), 59.37 (C-5'), 58.01 (OCH$_2$ propargyl), 17.36, 17.21, 16.90 and 16.73 (isopropyl CH$_{3s}$), 13.36, 12.92, 12.84 and 12.28 p.p.m. (isopropyl CH$_s$).

Compound C could be converted via various steps into cytidine and uridine monomers for the production of solid phase polymers.

EXAMPLE 5

Synthesis of 3',5'-O-(tetraisopropyldisiloxan-13-diyl)-2'-O-cyanomethyl-4-O-(2,6-dichlorophenyl)uridine (D):

The alkylation was carried out analogous to example 4 using bromoacetonitrile instead of propargylbromide. The title compound was obtained as a white foam in 55% yield, $R_f$ 0.51 on silica gel t.l.c. in petroleum ether/ethyl acetate (1:1 v/v). $^{13}C$ NMR spectrum (CDCl$_3$) δ: 169.91 (C-4), 154.57 (C-2), 144.54 (phenyl C-1), 143.96 (C-6), 128.69 (phenyl C-2 and C-6), 128.60 (phenyl C-3 and C-5), 127.12 (phenyl C-4), 115.72 (CN of cyanomethyl), 94.10 (C-5), 89.17 (C-1'), 82.34 (C-2'), 81.60 (C,4'), 67.27 (C-3'), 59.06 (C-5'), 55.82(CH$_2$ of cyanomethyl), 17.20, 17.08, 16.80 and 16.61 (isopropyl CH$_{3s}$), 13.23, 12.70 and 12.24 p.p.m. (isopropyl CH$_s$).

EXAMPLE 6

2'-O-propylation is best carried out by 2'-O-allylation followed by reduction of the allyl group. 2'-O-butylation is best carried out by 2'-O-crotylation (using crotylbromide and the process as described in example 4) followed by a reduction of the crotyl group.

EXAMPLE 7

3',5'-O-(tetraisopropyldisiloxan-1,3-diyl)-4-O-(2,6-dichlorophenyl)-uridine 14.65 g (60 mmol) dried uridine is dissolved in 150 ml anhydrous pyridine and the solution is cooled in an ice bath. A solution of 21 g (67 mmol) 1,3-dichloro-1,1,3,3-tetraisopropyldisiloxane in 10 ml dichloromethane is added to this over 15 minutes while stirring and excluding humidity. After the addition is completed, the mixture is stirred for a further 3 hours at room temperature; afterwards the complete conversion into a product of $R_f$ 0.58 is observed in a thin layer chromatogram (silica gel; mobile solvent chloroform/ethanol 9:1). The reaction is stopped by addition of 5 ml methanol and the mixture is evaporated in a vacuum. The residue is taken up in 200 ml dichloromethane and extracted twice with 200 ml 1 mol/l sodium bicarbonate solution in each case. The organic phase is dried over Na$_2$SO$_4$, filtered and evaporated in a vacuum. The residue is twice coevaporated in a vacuum with 25 ml toluene in each case whereafter a white foamy residue results. This is dissolved in 200 ml anhydrous 1,2-dichloroethane and 42 ml triethylamine (300 mmol) and 22.5 ml chlorotrimethylsilane (180 mmol) are added while stirring and excluding humidity. After a reaction time of 30 minutes a thin layer chromatogram (silica gel; petroleum ether/ethyl acetate 2:1) shows a complete conversion with a spot of $R_f$ 0.39. The reaction mixture is poured into 500 ml 1 mol/l sodium bicarbonate solution while stirring vigorously, the organic phase is separated and dried over $Na_2SO_4$. It is evaporated in a vacuum after filtration and the residue is coevaporated twice with 25 ml dry toluene in each case. The 2'-O-trimethylsilyl derivative obtained in this way is dissolved in 300 ml anhydrous dichloromethane and 42 ml triethylamine (300 mmol). 19.5 g 2-mesitylenesulphonyl chloride (90 mmol) and 1.8 g 4-dimethylaminopyridine (15 mmol) are added while stirring and excluding humidity. A complete conversion to a product with a $R_f$ 0.63 is observed in TLC (silica gel; petroleum ether/ethyl acetate 2:1) after a reaction time of 30 minutes. 1.35 g 1,4-diazabicyclo[2.2.2]octane (12 mmol) and 19.6 g 2,6-dichlorophenol (120 mmol) are added to the reaction solution and it is stirred for 2 hours at room temperature. After this time the conversion is complete as a TLC in petroleum ether/ethyl acetate 2:1 on silica gel shows ($R_f$ 0.56). The reaction mixture is stirred into 500 ml 1 mol/l Na bicarbonate solution, the organic phase is separated, dried over $Na_2SO_4$, filtered and evaporated in a vacuum. 2'-O-trimethylsilylether is obtained as an oily, viscous residue. The syrup is dissolved in 300 ml dichloromethane and a solution of 28.5 g p-toluene sulfonic acid monohydrate (150 mmol) in 100 ml tetrahydrofuran is added to this while stirring. After 2.5 minutes 28 ml triethylamine is added in order to neutralize the acid. Afterwards the reaction solution is poured into 500 ml 1 mol/l Na bicarbonate solution while stirring vigorously. The organic phase is separated, dried over $Na_2SO_4$ and the solvent is distilled off in a vacuum. The TLC (silica gel; petroleum ether/ethyl acetate 1:1) shows a spot with a $R_f$ 0.59 of 2,6-dichlorophenyl-2-mesitylenesulfonate and a further spot with a $R_f$ 0.41 of the desired product. The crude product is purified in several portions by preparative chromatography on silica gel using petroleum ether/ethyl acetate (2:1) as the eluant. After evaporating the fractions, 25.6 g corresponding to 67.5% of the theoretical yield is obtained as the pure final product.

$R_f$ value (silica gel; petroleum ether/ethyl-acetate 2:1) 0.23

$^{13}C$ NMR spectrum (CDCl$_3$) δ: 169.82 (C-4), 154.70 (C-2), 144.94 (C-6), 144.77 (phenyl-C-1), 128.92 (phenyl-C-2 and C-6), 128.71 (phenyl C-3 and C-5), 127.11 (phenyl C-4), 94.05 (C-5), 92.22 (C-1'), 82.01 (C-4'), 74.88 (C-2'), 68.89 (C-3'), 60.35 (C-5'), 17.40–16.85 (isopropyl-CH$_3$'s), 13.34, 12.91, 12.83 and 12.48 p.p.m. (isopropyl-CH's).

EXAMPLE 8

3',5'-O-(tetraisopropyldisilocan-1,3-diyl)-2'-O-allyl-4-O-(2,6-dichlorophenyl)uridine Tris(dibenzylidene-acetone)dipalladium(O) (0.183 g, 0.2 mmol) and 1,4-bis(diphenylphosphino)butane (0.341 g, 0.8 mmol) are suspended in dry tetrahydrofuran (40 ml) under an argon atmosphere. A solution of the compound produced according to example 7 (12.63 g, 20 mmol) and allylethylcarbonate (5.2 g, 40 mmol) in dry tetrahydrofuran (60 ml) are added and the mixture is heated for 30 minutes unter reflux. Thin layer chromatography (silica gel, mobile solvent petroleum ether/ethyl acetate, 2:1, v/v) is used to check that the reaction has run to completion. The reaction product is shown by a new band having a $R_f$ value of 0.48. After cooling the mixture is filtered and the solvent is removed in a vacuum. The reaction product is purified by preparative chromatography on silica gel with 3% ethyl acetate in dichloromethane as the mobile solvent.

After evaporating the fractions, 11 g (81.9% of the theoretical yield) of the final product is obtained.

$R_f$ value (silica gel thin layer chromatography; petroleum ether/ethyl acetate 2:1): 0.51

$^{13}C$ NMR spectrum (CDCl$_3$) δ: 169.61 (C-4), 154.49 (C-2), 144.64 (phenyl C-1), 144.37 (C-6), 134.29 (allyl CH), 128.75 (phenyl C-2 and C-6), 128.51 (phenyl C-3 and C-5), 126.93 (phenyl C-4), 116.85 (allyl=CH$_2$), 93.50 (C-5), 89.94 (C-1'), 81.64 (C-2'), 80.40 (C-4'), 70.90 (O—CH$_2$ of allyl), 67.49 (C-3'), 59.34 (C-5'), 17.24, 17.10, 16.79 and 16.63 (isopropyl CH$_3$s), 13.21, 12.83, 12.70 and 12.30 p.p.m. (isopropyl CH$_s$).

EXAMPLE 9

2'-O-allyl-4-O-(2,6-dichlorophenyl)uridine 5.5 g (8.19 mmol) of the compound produced according to example 8 is dissolved in 20 ml dry tetrahydrofuran and 1.1 mol/l tetrabutylammonium fluoride in 18 ml tetrahydrofuran is added while stirring. The reaction is completed after 5 minutes as shown by a thin layer chromatogram on silica gel using ethanol/chloroform (5:95 v/v) as the mobile solvent ($R_f$: 0.22).

The reaction is stopped with pyridine/methanol/water (50 ml, 3:1:1 v/v) and the solution is applied while stirring to the pyridine form of Dowex 50 Wx4-200 resin (30 g suspended in pyridine/methanol/water 50 ml 3:1:1 v/v). The mixture is stirred for 20 minutes, the resin is filtered off and washed with the above-mentioned solvent (3×50 ml). The combined filtrates and washing solutions are evaporated in a vacuum to dryness, taken up in toluene and evaporated again. The crude product is purified in 3 portions by preparative chromatography on silica gel with 6% ethanol in chloroform as the eluting agent. After evaporating the fractions in a vacuum, ethanol and pyridine residues are removed by addition of toluene and again evaporating in a vacuum at 45° C. After evaporation 2.91 g (82.9% of the theoretical yield) of the pure final product is obtained.

$R_f$ value (silica gel; ethanol/chloroform 1:4): 0.57

$^{13}C$ NMR spectrum (CDCl$_3$) δ: 169.74 (C-4); 155.28 (C-2), 146.20 (C-6), 144.42 (phenyl C-1), 133.54 (allyl CH), 128.67 (phenyl C-2 and C-6), 128.57 (phenyl C-3 and C-5), 127.13 (phenyl C-4), 117.98 (allyl=CH$_2$), 94.41 (C-5), 89.60 (C-1'), 84.54 (C-4'), 81.01 (C-2'), 71.10 (allyl CH$_2$O), 67.43 (C-3') and 59.55 p.p.m. (C-5').

EXAMPLE 10

2'-O-allyl-uridine 2.91 g (6.79 mmol) of the compound prepared according to example 9 is dissolved in 20 ml dry acetonitrile. 2.82 g (16.98 mmol) 2-nitrobenzaldoxime and 1.76 g (15.28 mmol) 1,1,3,3-tetramethylguanidine in 20 ml dry acetonitrile are added and the mixture is stirred for 18 hours at room temperature. A thin layer chromatogram on silica gel using ethanol/chloroform (1:4 v/v) as the mobile solvent shows that the reaction has run to completion ($R_f$ 0.37). The solvent is removed by evaporation in a vacuum and the remaining residue is dissolved in 100 ml dichloromethane and the product is extracted with 100 ml water. The aqueous phase is washed with 100 ml dichloromethane and subsequently with 100 ml diethyl ether. The slightly yellow aqueous phase is subsequently stirred for 5 minutes with the pyridine form of Dowex 50 Wx4-200 resin (25 g). The resin is removed by filtration and the turbid filtrate is washed twice with 50 ml dichloromethane and subsequently with 100 ml ether. The aqueous phase is evaporated in a vacuum. Traces of water are removed by addition of methanol and tetrahydrofuran and subsequently evaporation. The desired compound is crystallized from methanol, filtered off and washed with ether and dried. 1.83 g (94% of theory) of 2'-O-allyluridine is obtained.

$R_f$ value (silica gel; ethanol/chloroform 1:4 v/v): 0.39

$^{13}$C NMR spectrum (pyridine-d$_5$) δ: 164.48 (C-4), 151.72 (C-2), 140.76 (C-6), 135.11 (CH of allyl), 116.96 (allyl=CH$_2$), 102.17 (C-5), 88.26 (C-1'), 85.72 (C-4'), 82.57 (C-2'), 71.38 (allyl CH$_2$O), 69.41 (C-3') and 60.75 p.p.m. (C-5').

EXAMPLE 11

2'-O-allyl-uridine-5'-monophosphate 1.42 g 2'-O-allyl-uridine (5.0 mmol) is phosphorylated according to the method of Yoshikawa et al. (1967) Tetrahedron Lett. 50, 5065. The yield was 980 mg after chromatographic purification.

It was found that the use of trialkyl phosphate highly facilitated the phosphorylation with phosphoryl chloride. In addition 2',3'-O-isopropylidene nucleosides are moderately soluble in anhydrous trialkyl phosphates such as trimethyl and triethyl phosphates. These esters are useful solvents for phosphorylation. A 2',3'-O-isopropylidene nucleoside is added to a cold mixture of a trialkyl phosphate and phosphoryl chloride with stirring and was converted smoothly into the corresponding 5'-phosphorodichloridate in nearly quantitative yield. 5'-nucleotide was obtained by rapid hydrolysis of the chloridate group followed by removal of the isopropylidene group at 70° C.

EXAMPLE 12

2'-O-allyl-uridine-5'-diphosphate and -5'-triphosphate

In order to produce di- and triphosphates, 365 mg (1 mmol) of each of the monophosphates was reacted in each case with orthophosphoric acid and pyrophosphoric acid according to the method of Hoard and Ott (1965) J. Am. Chem. Soc. 87, 1785. The yields were 220 mg diphosphate and 140 mg triphosphate.

To a solution or suspension of the mono or oligonucleotide as the anhydrous tributylammonium salt in DMF was added 1,1'-carbonyldimidazol in DMF. The mixture in a tightly stoppered container was shaken for 30 min. held in a dissicator at room temperature for 4 hrs. or overnight and then treated with methanol. After 30 min. at room temperature, tributylammonium pyrophosphate in DMF was added with rigorous mixing and the stoppered mixture was held at room temperature in a dissicator for 1 day. The imidazolium pyrophosphate precipitate was removed and washed with DMF by centrifugation.

The supernatant was treated with an equal volume of methanol, and the solution was evaporated under vacuum to dryness. The residue was chromatographed on a DEAE-cellulose column with a linear gradient of triethylammonium bicarbonate pH 7.5. Diphosphates are here resolved from triphosphates by chromatography. Appropriate factions were evaporated under vacuum and the triethylammonium bicarbonate was removed by addition and evaporation of ethanol.

All 5'-phosphates were characterized by means of elementary analysis, electrophoresis and $^{31}$P-NMR spectroscopy.

It will be understood that the specification and examples serve to illustrate but do not limit the present invention. Other embodiments within the spirit and scope of the invention will suggest themselves to those skilled in the art.

---

---

We claim:

1. A nucleotide of formula I,

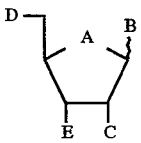

I wherein

B is a purine or pyrimidine base

A is oxygen

C is —O—R wherein R is an alkyl group with a total of at least 2 C atom or an alkenyl group or an alkynyl group having at least 2 C atoms wherein the alkyl, alkenyl or alkynyl groups are unsubstituted or substituted by at least one halogen, cyano, carboxy, hydroxy, nitro or mercapto, group and D and E are groups selected from the group consisting of OH, —PO$_4$H$_2$, —P$_2$O$_7$H$_3$, —P$_3$O$_{10}$H$_4$, and reactive groups which form 3'-5' internucleotide bonds.

2. The nucleotide claim 1 wherein D and E are selected from the group consisting of OH, —PO$_4$H$_2$, P$_2$O$_7$H$_3$, and —P$_3$O$_{10}$H$_4$.

3. The nucleotide of claim 1 wherein the reactive group is a phosphoramidite.

4. The nucleotide of claim 1 which is 3',5'-O-(tetraisopropyldisiloxane-1,3-diyl)-2'-O-propargyl-4-O-(2,6-dichlorophenyl)uridine.

5. The nucleotide of claim 1, wherein the purine or pyrimidine base is selected from the group consisting of adenine-9-yl, cytosine-1-yl, guanine-9-yl, uracil-1-yl, hypoxanthine-9-yl and thymine-1-yl.

6. The nucleotide of claim 1, wherein the purine or pyrimidine base is a 2-aminoadenine-9-yl residue.

7. The nucleotide of claims 1 or 5, wherein the alkenyl residue is an alk-2-enyl residue.

8. The nucleotide of claims 1 or 5 wherein the alkenyl residue is an allyl residue.

9. The nucleotide monomer of claims 1 or 5 consisting of 2'-O-allyl-4-0(2,6-dichlorophenyl) uridine.

10. The nucleotide monomer of claims 1 or 5 selected from the group consisting of 2'-O-allyl-uridine-5'-monophosphate, 2'-O-allyl-adenosine-5'-monophosphate, 2'-O-allyl-guanosine-5'-monophosphate, 2'-O-ally-cytidine-5'-monophosphate, 2'-O-allyl-thymidine-5'-monophosphate, and 2'-O-allyl-inosine-5'-monophosphate.

11. A composition comprising a nucleotide oligomer or a nucleotide polymer wherein said nucleotide oligomer or said nucleotide polymer comprises the nucleotide monomer of claim 10.

12. The nucleotide monomer of claims 1 or 5 selected from the group consisting of (2'-O-allyl-uridine-5'-diphosphate or -5'-triphosphate), (2'-O-allyl-adenosine-5'-diphosphate or -5'-triphosphate), (2'-O-allyl-guanosine-5'-diphosphate or -5'-triphosphate), (2'-O-allyl-thymidine-5'-diphosphate or -5'-triphosphate), (2'-O-allyl-cytidine-5'-diphosphate or -5'-triphosphate), and (2'-O-allyl-inosine-5'-diphosphate or -5'-triphosphate).

13. A composition comprising a nucleotide oligomer or a nucleotide polymer wherein said nucleotide oligomer or said nucleotide polymer comprises the nucleotide monomer of claim 12.

14. A nucleotide polymer containing at least one of the monomers as claimed in claims 1 or 5.

15. A composition comprising the nucleotide polymer of claim 14 in a carrier.

16. A nucleotide polymer comprising at least one monomer of claim 1 and having the following formula II

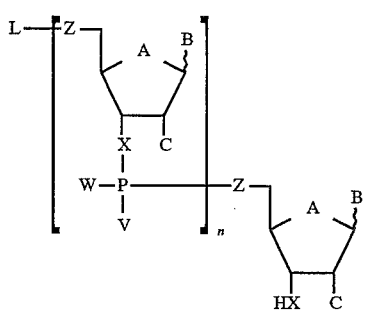

wherein X and Z are O, V and W are O or S, and wherein V and W can be the same or different in a monomer unit, L is H or a partner of an antigen-antibody or biotin-avidin or streptavidin binding pair, and B, A and C have the meaning defined in claim 1 and n denotes an arbitrary whole number greater than one.

17. The nucleotide polymer of claim 16 having a 3'-terminal end wherein the 3'-terminal end is a 3'-deoxyribonucleoside.

18. A composition comprising the nucleotide polymer of claim 16 in a carrier.

19. The nucleotide polymer of claim 16, wherein L is biotin.

20. The nucleotide polymer of claim 19 having a 3'-terminal end wherein the 3'-terminal end is a 3'-deoxyribonucleoside.

21. A composition comprising the nucleotide polymer of claim 19 in a carrier.

22. An oligonucleotide consisting of SEQ ID NO: 1, wherein said oligonucleotide comprises at least one modified nucleoside having a 2'-O-allyl moiety.

23. A method for detecting the presence of a nucleic acid molecule in a sample comprising:

a) incubating said sample with a nucleic acid probe which hybridizes to said nucleic acid molecule and which comprises at least one nucleotide of claim 1, wherein said incubation is under conditions where hybridization takes place; and b) detecting hybridization of said nucleic acid probe to said nucleic acid molecule as an indication of the presence of said nucleic acid molecule in said sample.

* * * * *

UNITED STATES PATENT AND TRADEMARK OFFICE
CERTIFICATE OF CORRECTION

PATENT NO. : 5,658,731
DATED : Aug. 19, 1997
INVENTOR(S) : Sproat et al.

It is certified that error appears in the above-identified patent and that said Letters Patent is hereby corrected as shown below:

In cover page, in the section entitled Other Publications, line 3, change "773-892" - - 733- 738 - -.
In cover page, in the section entitled Other Publications, line 1, change "113-129" to- - 113- 128 - -.
In column 1, line 20, change "an" to - - a - -.
In column 2, line 40, change "modified" to - - be modified - -.
In column 3, line 49, change "above" to - - Above - -.
In column 9, line 9, change "hinds" to - - binds - -.
In column 10, line 27, change "13-diyl" to - - 1,3-diyl - -.
In column 11, line 59, change "unter" to - - under - -.

Signed and Sealed this

Eighth Day of May, 2001

Attest:

NICHOLAS P. GODICI

Attesting Officer

Acting Director of the United States Patent and Trademark Office